(12) United States Patent
Sanders

(10) Patent No.: US 8,428,333 B2
(45) Date of Patent: Apr. 23, 2013

(54) APPARATUS FOR PERFORMING REPETITIVE OPERATIONS

(75) Inventor: Johanna Helena Maria Sanders, Nijmegen (NL)

(73) Assignee: Vefin N.V., Curacao (NL)

( * ) Notice: Subject to any disclaimer, the term of this patent is extended or adjusted under 35 U.S.C. 154(b) by 1143 days.

(21) Appl. No.: 12/293,047

(22) PCT Filed: Mar. 16, 2006

(86) PCT No.: PCT/NL2006/050057
§ 371 (c)(1),
(2), (4) Date: Dec. 5, 2008

(87) PCT Pub. No.: WO2007/105938
PCT Pub. Date: Sep. 20, 2007

(65) Prior Publication Data
US 2010/0232716 A1     Sep. 16, 2010

(51) Int. Cl.
*G06K 9/00* (2006.01)
(52) U.S. Cl.
USPC ........................................ 382/141; 270/1.03
(58) Field of Classification Search ................ 382/111, 382/112, 141; 356/429; 226/10, 27, 45; 234/2; 270/1.03, 52.02
See application file for complete search history.

(56) References Cited

U.S. PATENT DOCUMENTS

| 4,600,841 | A | | 7/1986 | Tokuno et al. | 250/548 |
| 5,305,392 | A | * | 4/1994 | Longest, Jr. et al. | 382/8 |
| 6,266,437 | B1 | * | 7/2001 | Eichel et al. | 382/149 |
| 2003/0001042 | A1 | | 1/2003 | Betti et al. | 242/527 |
| 2003/0066451 | A1 | | 4/2003 | Mengisen et al. | 101/485 |

FOREIGN PATENT DOCUMENTS

| DE | 19855177 A1 | 6/2000 |
| EP | 1080887 A1 | 3/2001 |
| WO | WO 97/29453 A1 | 8/1997 |
| WO | WO 01/64563 A2 | 9/2001 |

OTHER PUBLICATIONS

Notification of the First Office Action, dated Apr. 15, 2010, State Intellectual Property Office of the People's Republic of China.
Office Action issued for European Patent Application No. 06716690.0, Feb. 21, 2012.
Written Opinion of the European Patent Office in counterpart foreign application No. PCT/NL2006/050057 filed Mar. 16, 2006.
Official Search Report of the European Patent Office in counterpart foreign application No. PCT/NL2006/050057 filed Mar. 16, 2006.

* cited by examiner

*Primary Examiner* — Andrew W Johns
(74) *Attorney, Agent, or Firm* — Steven M. Koehler; Westman, Champlin & Kelly, P.A.

(57) ABSTRACT

The invention pertains to a apparatus for performing operations, in particular cutting, embossing, creasing, folding and/or sealing, on a moving web provided with a series of identical images, which apparatus comprises a sensor for at least partially detecting the images on the web, and a processing unit which, dependent on a comparison of the data obtained with the sensor and a reference, generates an output signal to be used for one or more of the said operations. The processing unit comprises a memory and is arranged to select at least part of the detected data, store the selected data in the memory, and utilize the selected data as the reference. The invention further pertains to module for performing operations on a moving web and method of generating an output signal.

11 Claims, 1 Drawing Sheet

APPARATUS FOR PERFORMING REPETITIVE OPERATIONS

CROSS-REFERENCE TO RELATED APPLICATION

This application is a Section 371 National Stage Application of International Application PCT/NL2006/050057 filed Mar. 16, 2006 and published as WO 2007/105938 in English.

BACKGROUND

The discussion below is merely provided for general background information and is not intended to be used as an aid in determining the scope of the claimed subject matter.

Aspects of the invention relate to an apparatus for performing operations, in particular cutting, embossing, creasing, folding and/or sealing, on a moving web, typically of paper, cardboard or laminated material and provided with images, typically a series of identical images, which apparatus comprises a sensor for at least partially detecting the images on the web, and a processing unit which, dependent on a comparison of data obtained with the sensor and a reference, generates an output signal to be used for one or more of the said operations. The invention further relates to a module for use in the said apparatus, to a method of generating an output signal to be used for one or more apparatus operations, and to a roll of web material.

As explained in international patent application WO 97/29453, it is already known in the art to control processing operations on a moving material strip by means of control marks printed-on the strip, which marks can be detected by photocells or other optical devices. The marks are usually printed in a color tone which contrasts with the surroundings, thus enabling the detection means to detect the exact position of e.g. printed patterns and defining the current position of the material strip. This information can serve e.g. to ensure that subsequently applied crease line patterns coincide with the printed patterns and that the folding of the material takes place along these crease lines.

U.S. Pat. No. 4,600,841 relates to a mark detector for detecting marks on a running web distinguished from any printed letter or pattern or any printing smudge. The width of mark segments and the distance between them are determined and, if they are within preset ranges, a mark detection signal is given. A delayed signal generator and a false signal generator are provided.

DE 33 32 750 relates to a color mark probe, which is constructed in such a way that both the balancing on the background of the material to be scanned and the bright/dark switchover can be performed fully electronically from outside without operating actions.

The presence of control marks in the end product, be it a carton holding a liquid or sachets containing a powder, is generally undesirable. Hence, control marks are usually kept relatively small and are located e.g. on the bottom of a carton or on the seals of a sachet.

SUMMARY

This Summary and the Abstract herein are provided to introduce a selection of concepts in a simplified form that are further described below in the Detailed Description. This Summary and the Abstract are not intended to identify key features or essential features of the claimed subject matter, nor are they intended to be used as an aid in determining the scope of the claimed subject matter. The claimed subject matter is not limited to implementations that solve any or all disadvantages noted in the background.

To this end, the apparatus according to an aspect of the invention is characterised in that the processing unit comprises a memory and in that the processing unit is arranged to select at least part of the detected data, store the selected data in the memory, and utilize the selected data as the reference. It is preferred that the web is provided with decorative images, i.e. images which are not primarily intended to facilitate synchronization of apparatus operations, and that the processing unit is arranged to select the data from these decorative images.

Thus, no control marks are required and the apparatus need not be programmed anew when a web provided with different marks is used on the apparatus. Although marks may of course still be present, the apparatus can select one or more parts of the images already present on the web.

The invention further pertains to a module for use in a apparatus for performing operations, in particular cutting, embossing, creasing, folding and/or sealing, on a moving web provided with a series of identical images, which module i) comprises an input to be connected to a sensor for at least partially detecting the images on the web and a memory and ii) is arranged to select at least part of data received at the input, store the selected data in the memory, utilize the selected data as a reference, and, dependent on a comparison of the data obtained with the sensor and the reference, generate an output signal to be used for one or more of the said operations.

This module can be built into existing apparatuses, thus allowing such apparatuses to employ more materials, i.e. both materials provided with control marks and materials that comprise no control marks at all.

It is preferred that the sensor is arranged to detect a specific width of the images and that the apparatus respectively module comprises a converter that is arranged to determine average densities over at least part of this width. By averaging over a specific width, preferably in a range from 0.2 to 10 mm, more preferably in a range from 0.3 to 4 mm, sensitivity to (unintended) variations in the images or lateral shifting of the web is further reduced.

In a further embodiment, the converter is arranged to divide the images, in a direction of processing, into sections and to generate a digital representation of the images based on the average density of the sections. For instance, a "0" or "1" is allocated to each section dependent on whether or not the average density exceeds a predetermined threshold value.

The invention further pertains to a method of generating an output signal to be used for one or more apparatus operations, in particular cutting, embossing, creasing, folding and/or sealing, on a moving web and to a roll of web material for use in the above-described device or method, which material has been provided with a series of identical decorative images, preferably printed decorative images, and is free of control marks for the said apparatus operations. It is preferred that the web material comprises separating zones preferably free of any images or marks and/or preferably marked of against the decorative images.

It is further preferred that the web material comprises a laminate having weight of at least 200 g/m².

Within the framework of the present invention, the words "decorative images" denote images that serve to make the end product, e.g. a package, look more attractive and/or contain commercial information, such as a brand or barcode, and/or contain other information not intended to facilitate or enable performing operations, in particular cutting, embossing, creasing, folding and/or sealing, on a moving web.

BRIEF DESCRIPTION OF THE DRAWING

The invention will now be explained in more detail with reference to the drawings, which schematically show a preferred embodiment of the present apparatus and module.

It is noted that the drawings are not to scale and that details, which are not required for understanding the present invention, may have been omitted. Terms as "higher", "lower", "upwards", "downwards", and the like relate to the embodiments as oriented in the figures. Further, elements that are at least substantially identical or that perform an at least substantially identical function are denoted by the same numeral.

DETAILED DESCRIPTION OF THE ILLUSTRATIVE EMBODIMENT

Figure 1:
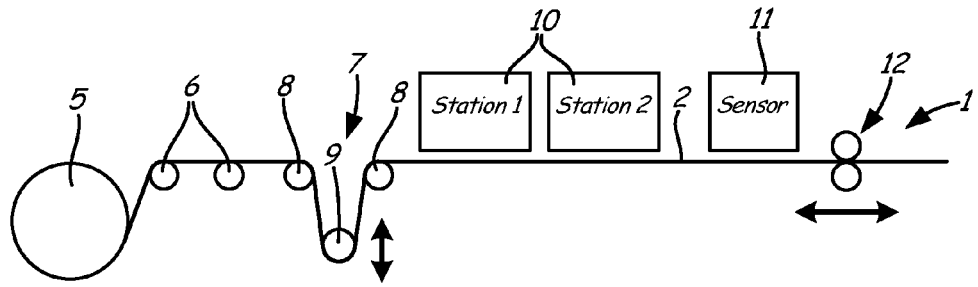
FIG. 1 shows a side view of a apparatus for performing operations on a moving web.
Figure 2:
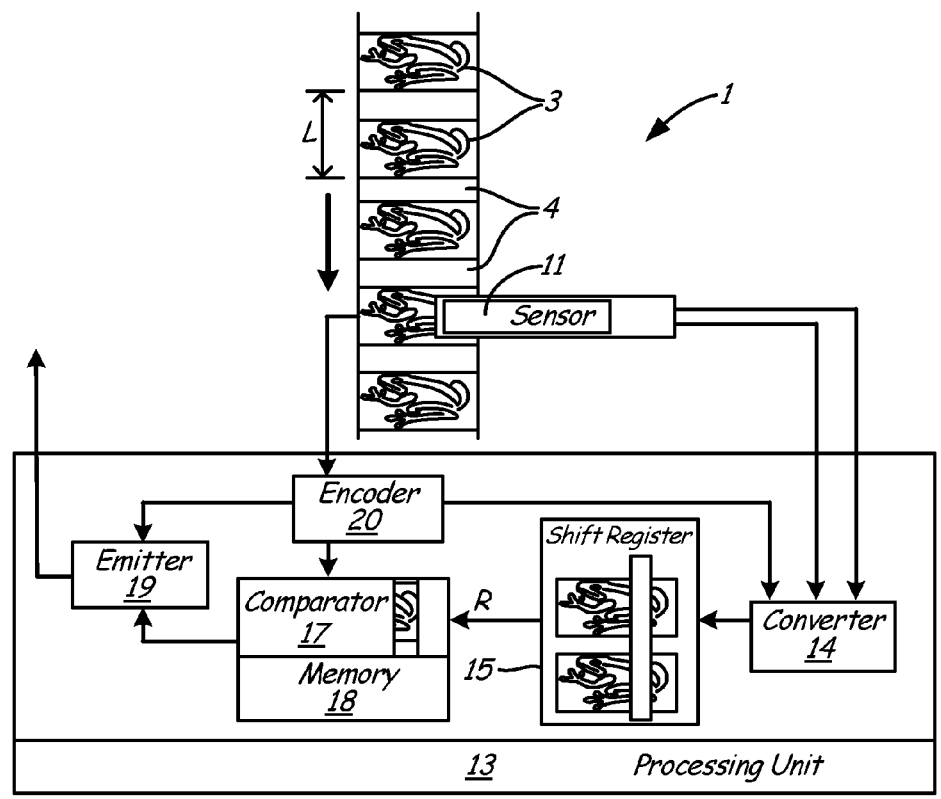
FIG. 2 shows a front view of a moving web and a sensor as well as a module according to an aspect of the present invention for use in the apparatus according to FIG. 1.

FIG. 1 and the upper half of FIG. 2 schematically show a packaging apparatus 1, known in itself, which performs mechanical operations, in particular cutting, embossing, creasing, folding, and/or sealing, on a moving continuous web 2, typically of paper, cardboard or laminated material. The web 2 is provided with a series of identical images 3, which, in this example, are separated by relatively narrow zones 4 free of any images or marks and spanning e.g. 2 to 100 mm in a direction of processing (often also referred to as "MD"). The apparatus 1 is provided with a roll 5 of the web material, which material is guided via rollers 6 to a positioning device 7, comprising e.g. two stationary rollers 8 and one adjustable roller 9. This latter roller 9 can be moved to the left or to the right (as indicated by an arrow) thus positioning the moving web 2 slightly higher respectively lower (FIG. 2). Downstream of the positioning device 7, the apparatus 1 comprises one or more stations 10 for performing operations, e.g. a station for applying so-called pull taps, and a station for folding the web 2 about a longitudinal axis and sealing the edges of the web 2 together thus forming a tube and a station for filling the tube with e.g. a liquid or a powder. The apparatus 1 further comprises an optical sensor 11 for at least partially detecting the images 3 on the web 2 and one or more further stations, e.g. a station 12 for cutting and sealing the tube e.g. to form cartons filled with a liquid or sachets filled with a powder, which latter station 12 can be moved up and down (as indicated by an arrow).

The lower half of FIG. 2 shows a processing unit 13 in accordance with the present invention, which unit 13 is part of the apparatus 1. Integrated in the processing unit 13 are at least a converter 14 connected to a shift register 15, which in turn is connected to a comparator 17 comprising a memory 18. The comparator 17 is connected to a signal emitter 19. A digital clock, in this case a generally known Gray encoder 20, which can either be part of the apparatus 1 or of be integrated in the processing unit, is connected to one or more of the moving parts of the apparatus 1, typically to the main driving shaft (not shown). Outputs of the encoder 20 are connected to the comparator 17 and the signal emitter 19 and to the converter 14. In this example, one revolution of the main driving shaft equals the length of two objects (2 L), i.e. the sum of the lengths of two images 3 and two separating zones 4. Further, one revolution is divided in 256 Gray codes of 8 bits each and, consequently, the length (L) of one object corresponds to 128 Gray codes.

During operation and after a new roll has been fed to the apparatus in a manner commonly known, the optical sensor 11 detects the images 3 on the web 2 over a specific width, preferably a width in a range from 0.3 to 4 mm, for instance 0.7 mm. The signal from the sensor 11 is fed to the converter 14, which divides the signal (representing the images), into sections, also referred to as density points. The converter 14 then calculates an average density for each section and digitizes the signal based on the average density of each of the sections. In this example, digitizing is achieved by allocating a "0" or "1" to each section dependent on whether or not the average density exceeds a set threshold value, e.g. the overall average of one image 3. The digitized signal is fed to the shift register 15, which selects from the signal a sequence, of, in this example, 128 density points, which represents a length L of one object. As a matter of course, it is also possible to select a sequence, which represents only part of the length L of one object.

After a sequence has been selected, this sequence is stored in a first memory block of the memory 18 and the digitized signal is checked for an identical or substantially identical sequence, so as to confirm the suitability of the selected sequence to serve as a reference sequence. When a reference sequence, e.g. 0001110100110 . . . 000 wherein the first three bits and the last three bits represent half a separating zone 4 on either end of an image 3 and the very last bit represents the end of an object, has been selected and confirmed, this sequence is stored in a second memory block of the memory 18. Subsequent sequences are fed to the comparator 17 and compared to the reference sequence in the second block. When it is established, based on this comparison, that a sequence has been completed, i.e. that the divide between two objects has been reached, a pulse is fed to the signal emitter 19. In the emitter 19, the timing of this pulse is compared to the timing of the apparatus by means of the Gray codes, i.e. the reference sequence provides the position of the end of the present object on the web, whereas the Gray codes provide the angular position of the apparatus and hence the position where the end of the present object ought to be. If these positions are asynchronous, the position of the web 2 and/or of the apparatus 1 is slightly advanced or delayed by adjusting the position of respectively the adjustable roller 9 or the station 12 (in accordance with the arrows). E.g. if the web 2 is late the adjustable roller 9 or one of the stations (12) is moved upwards.

In other words, the output signal of the signal emitter 19 is employed to synchronize the apparatus processes and the movement of the web.

It is preferred that, when a deviation is detected, this deviation is stored in a third memory block of the memory 18 and that subsequent sequences are compared to the stored deviation as well. If these sequences correspond to the deviation, the deviation will be utilized as the reference sequence.

The above-described apparatus and method function very reliably and will generate a proper output signal, even if up to e.g. 2%, 5%, or 10%, depending on specifications of the product, of the bits in one or more of the sequences deviate from the reference sequence (thus providing a certain tolerance and, for instance, enabling the apparatus to absorb incidental minor printing errors on the web).

Automatic printing quality control, during the processing of the web in the apparatus, and automatic rejection by the apparatus of undesirable deviations of the printed images, can be enhanced if the processing unit of the apparatus is programmable to reject pre-selected deviations in the images or densities on the web or to accept only a limited number of images. To that end, e.g. a programming unit (not shown) is connected or connectable (in case of an external programming unit) to the output of the converter 14.

Further, it was found that the apparatus, once it has shifted into pre-production mode, will typically confirm a reference sequence after only two to five objects have passed, which number corresponds to the number of objects that is normally lost during start up.

From the above explanations, it will be clear that the apparatus, the module and the method according to the present invention require no dedicated control marks. Instead, one or more parts of images already present on the web are effectively selected as a reference for synchronizing mechanical operations on the web. Put differently, the images already present on the web are no longer considered an obstacle (noise) to detecting a control mark, but instead are employed as a source of information which itself is in most cases sufficient to synchronize operations on the web.

Although the above-described embodiments employ an integrated processing unit, it is also possible to use a module 13, which comprises the same components as the processing unit. Such a module can be built into existing apparatuses and preferably generates the same output signals as the device or unit it replaces or supplements, thus allowing these apparatuses to employ more materials, i.e. both materials provided with control marks and materials that comprise no marks at all.

The invention is not restricted to the above-described embodiments, which can be varied in a number of ways within the scope of the claims. For instance, instead of employing one sensor, it is also possible to employ two or more sensors yielding, in the example above, 256 (two for each Gray code) or more density points for each object.

The invention claimed is:

1. An apparatus for performing cutting, embossing creasing, folding and/or sealing, on a moving web provided with a series of identical images, which apparatus comprises a sensor for at least partially detecting the images on the web, and a processing unit which, dependent on a comparison of data obtained with the sensor and a reference (R), generates an output signal to be used for one or more of the said operations, wherein the processing unit comprises a memory and in that the processing unit is arranged to select at least part of the detected data, store the selected data in the memory, and utilize the selected data as the reference (R), and wherein the processing unit is arranged, if data obtained with the sensor deviates from the reference (R), to store such deviation data in the memory and, if such deviation data occurs again, to utilize the deviation data as the reference (R).

2. The apparatus according to claim 1, wherein the web is provided with a series of identical decorative images and wherein the processing unit is arranged to select the data from these decorative images.

3. The apparatus according claim 1, wherein the sensor is arranged to detect a specific width of the images and wherein the module comprises a converter that is arranged to determine average densities over at least part of this width.

4. The apparatus according to claim 3, wherein the converter is arranged to divide the images, in a direction of processing, into sections and to generate a digital representation of the images based on the average density of the sections.

5. The apparatus according to claim 1, further comprising a clock, which is connected to one or more of the moving parts of the apparatus and which generates a signal based on the rotation or translation of such part(s).

6. A module for use in a apparatus for performing cutting, embossing, creasing, folding and/or sealing, on a moving web provided with a series of identical images, which module comprises:
   an input to be connected to a sensor for at least partially detecting the images on the web;
   a memory; and
   is arranged to select at least part of the data received at the input, store the selected data in the memory, utilize the selected data as a reference (R), and, dependent on a comparison of the data obtained with the sensor and the reference (R), generate an output signal to be used for one or more of the said operations, and, if data obtained from the sensor deviates from the reference (R), to store such deviation data in the memory and, if such deviation data occurs again, to utilize the deviation data as the reference (R).

7. A method of generating an output signal to be used for one or more apparatus operations comprising cutting, embossing, creasing, folding and/or sealing, on a moving web provided with a series of identical images, which method comprises:
   at least partially detecting the images on the web,
   selecting at least part of the detected data,
   storing the selected data in a memory as a reference (R),
   generating, dependent on a comparison of subsequently obtained data and the reference (R), the said output signal, and
   if data obtained from the sensor deviates from the reference (R), to storing such deviation data in the memory and, if such deviation data occurs again,
   utilizing the deviation data as the reference (R).

8. The method according to claim 7, wherein the web comprises a series of identical decorative images and wherein the data is selected from these decorative images.

9. The method according to claim 8, wherein the image detected by the sensor has a length (L), which is equal to the sum of the length of a group of images belonging together and zones separating the images of the group, and another zone separating the group of images and a next group of images.

10. The method according to claim 8, wherein the image detected by the sensor has a length (L), which is equal to the sum of the length of an image and a zone separating that image from the next image.

11. The method according to claim 7, wherein the images are divided, in a direction of processing, into sections and a digital representation of the images is generated based on the average density of the sections.

\* \* \* \* \*

UNITED STATES PATENT AND TRADEMARK OFFICE
CERTIFICATE OF CORRECTION

PATENT NO.        : 8,428,333 B2                                        Page 1 of 1
APPLICATION NO. : 12/293047
DATED             : April 23, 2013
INVENTOR(S)       : Johanna Helena Maria Sanders It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1219 days.

Signed and Sealed this
Eighth Day of September, 2015

Michelle K. Lee
*Director of the United States Patent and Trademark Office*